United States Patent [19]

Love et al.

[11] Patent Number: 5,559,265

[45] Date of Patent: Sep. 24, 1996

[54] ASHLESS ANTIOXIDANT LUBRICATING OIL ADDITIVE

[75] Inventors: Doris Love, Fishkill; Alison E. Hadowanetz, Maybrook, both of N.Y.

[73] Assignee: Ethyl Additives Corporation, Richmond, Va.

[21] Appl. No.: 481,207

[22] Filed: Jun. 7, 1995

Related U.S. Application Data

[63] Continuation of Ser. No. 274,106, Jul. 12, 1994, abandoned, which is a continuation of Ser. No. 708,262, May 28, 1991, abandoned.

[51] Int. Cl.$^6$ ................................................. C07F 9/165
[52] U.S. Cl. ............................... 558/177; 508/224 ECW
[58] Field of Search .............................................. 558/177

[56] References Cited

U.S. PATENT DOCUMENTS

| | | | |
|---|---|---|---|
| 2,895,984 | 7/1959 | McCall et al. | 558/105 |
| 3,004,996 | 10/1961 | Arakelian et al. | 558/105 |
| 3,341,633 | 9/1967 | Asseff | 558/105 |
| 3,654,154 | 4/1972 | Braid | 558/105 |

*Primary Examiner*—Johann Richter
*Assistant Examiner*—Michael G. Ambrose
*Attorney, Agent, or Firm*—Dennis H. Rainear

[57] ABSTRACT

A method for producing an ashless, antioxidant lubricating oil additive. The method comprises:

(a) reacting an alcohol with phosphorus pentasulfide to form a dithiophosphoric acid intermediate;

(b) treating the dithiophosphoric acid intermediate with an expoxide to yield a corresponding dithiophosphoric ester alcohol product; and (c) recovering the dithiophosphoric ester alcohol product lubricant oil additive.

6 Claims, No Drawings

ASHLESS ANTIOXIDANT LUBRICATING OIL ADDITIVE

This is a continuation of patent application Ser. No. 08/274,106, filed on Jul. 12, 1994 now abandoned, which is a continuation of patent application Ser. No. 07/708,262, filed May 28, 1991 now abandoned.

BACKGROUND OF THE INVENTION

This invention is related to lubricating oils, and more particularly to an ashless, antioxidant lubricating oil additive.

In developing lubricating oils there have been many attempts of providing additives which impart antioxidant properties in the lubricating oils. Zinc dithiophosphates have been used in formulated motor oils as antioxidant additives for more than fifty years. However, zinc dithiophosphates give rise to ash which contributes to particulate matter found in automotive exhaust emissions. It is important to limit the particulate matter formed during engine use for toxicological and environmental reasons, but it is equally important to maintain undiminished antioxidant properties of the lubricating oil.

Thus, it is an object of this invention to provide an ashless, antioxidant additive which imparts these desired properties to a lubricant.

DISCLOSURE STATEMENT

U.S. Pat. No., 2,568,784 discloses a method of producing reaction products of olefine oxides and phosphoric anhydride or phosphorus pentasulfide and the method of forming the same. The reaction products are prepared by reacting either phosphoric anhydride or phosphorus pentasulfide with an olefine oxide.

U.S. Pat. No. 3,197,4.04 discloses a method of producing reaction products of phosphorus pentasulfide with epoxides and metal salts thereof. These reaction products and salts are useful in lubricating oil compositions.

U.S. Pat. No. 3,346,667 discloses a reaction product produced from a phosphorus oxide or sulfide, an oxirane compound and a hydroxy or thiol compound together. These products are useful in synthetic plastics.

U.S. Pat. No. 4,834,893 discloses phosphorodithioate substituted carboxylic anhydride or acid derivates and their corresponding metal salts have been found to be effective multifunctional additives for various lubricants and fuels.

SUMMARY OF THE INVENTION

This invention provides a method to produce an ashless, antioxidant lubricating oil additive. The method comprises:

(a) reacting an alcohol with phosphorus pentasulfide to form a dithiophosphoric acid intermediate;

(b) treating the dithiophosphoric acid intermediate with an expoxide to yield a corresponding dithiophosphoric ester-alcohol product; and (c) recovering the dithiophosphoric ester-alcohol product lubricating oil additive.

DETAILED DESCRIPTION OF THE INVENTION

The present invention relates to the use of ashless antioxidant agents in lubricating oils to reduce the ash content of the formulation. The ashless materials will be used as a partial replacement for the zinc dithiophosphates currently used for antioxidant purposes.

Up to the present time, dithiophosphoric acids have not been reacted with epoxides to yield a product with antioxidant properties.

According to the present invention, an ashless, antioxidant lubricating oil additive is produced by the method which comprises:

(a) reacting an alcohol with phosphorus pentasulfide to form a dithiophosphoric acid intermediate;

(b) treating the dithiophosphoric acid intermediate with an expoxide to yield a corresponding dithiophosphoric ester-alcohol product; and (c) recovering the ester alcohol product lubricating oil additive.

In the present method, and as shown in the equations below, an alcohol is reacted with phosphorus pentasulfide in a ratio of about 4:1 but could be a ratio of about 3:1 to about 5:1, to give the corresponding dithiophosphoric acid. The dithiophosphoric acid is then reacted with an epoxide in a ratio of about 1:1 about but could be a ratio of about 0.5:1 to 1.5:1 to give the corresponding ester-alcohol derivatives (i.e., the ester alcohol product).

The equations for the reactions are as follows:

(a) $4ROH + P_2S_5 \longrightarrow 2(RO)_2-\underset{\underset{SH}{\|}}{P}=S \uparrow + H_2S$ (Alcohol)  (Phosphorus Pentasulfide)   (Dithiophosphoric acid)

(b) $2(RO)_2-\underset{\underset{SH}{\|}}{P}=S + R'-CH\underset{O}{\overset{}{\diagdown\!\diagup}}CH_2 \longrightarrow$ (Dithiophosphoric acid)   (Epoxide)

$(RO)_2-\underset{\underset{S}{\|}}{P}-S-CH_2-\underset{\underset{OH}{|}}{CH}-R'$ (Dithiophosphoric Ester-Alcohol Product) +

$(RO)_2-\underset{\underset{S}{\|}}{P}-S-\underset{\underset{R'}{|}}{CH}-CH_2OH$ wherein R is a ($C_1$–$C_{40}$) alkyl group and R' is $CH_3(CH_2)_x$ where X is a value of about 1 to about 40.

According to the present invention and as illustrated in the above equations, in the preparation of the dithiophosphoric acid, initially, an alcohol or mixture of alcohols was added to a slurry of $P_2S_5$ in heptane at 70° C. (158° F.). The mole ratio of alcohol to $P_2S_5$ was about 4:1 but could be in a range of about 5:1 to about 3:1. The mixture is stirred 1 hour at 70° C. and then three hours at 80° C. The unreacted $P_2S_5$ was then filtered off.

The dithiophosphoric acid or a mixture of dithiophosphoric acids was then combined with the epoxide at ambient temperature in a ratio of 1:1 but could be in a ratio of 0.5:1 to 1.5:1. The mixture was stirred at 90° C. for three hours, vacuum stripped and filtered.

In order to illustrate and show the advantages of the present invention, the following examples are provided. In Examples I and II, the preparations are set forth in steps (e.g., A, B, etc).

EXAMPLE I

Preparation Of Dithiophosphoric Ester Alcohol From 2-Octanol, $P_2S_5$ and a $C_{18}$ Epoxide

A) Synthesis Of Dithiophosphoric Acid 572 gms. (4.4 m) of 2-octanol was added over ½ hour to a slurry of 222 gms. (1.0 m) of $P_2S_5$ in 400 ml. heptane at 65°–70° C. under an $N_2$ Blanket. The reaction mixture was then stirred at 70° C. for 1 hour and at 80° C. for three hours, and then filtered free of unreacted $P_2S_5$ to yield 1024 gms. (2.0 m) of dithiophosphoric acid with a neutralization number of 108 (Theory:110).

B) Synthesis Of Dithiophosphoric Ester-Alcohol From The Dithiophosphoric Acid Prepared in (A)

128.0 gms. (0.2 m) dithiophosphoric acid prepared in A was combined with 67.0 gms. (0.25 m) of a $C_{18}$ Epoxide at ambient temperature. The reaction mixture was stirred at 90° C. for three hours, vacuum stripped and filtered to yield 149 gms. (Theory:155 gms.) of the dithiophosphoric ester-alcohol.

| Test | Found | Theory |
| --- | --- | --- |
| % S | 9.3 | 10.3 |
| % P | 4.9 | 5.0 |

EXAMPLE II

Preparation Of Dithiophosphoric Ester-Alcohol From Isopropyl Alcohol, $P_2S_5$ And a $C_{18}$ Epoxide

A. Synthesis of Dithiophosphoric Acid (L-189-5146)

264 gms. (4.4 m) of Isopropanol was added over ½ hour to a slurry of 222 gms.(1.0 m) of $P_2S_5$ in 400 ml. of heptane at 65°–70° C. under a $N_2$ blanket. The reaction mixture was then stirred at 70° C. for one hour and at 80° C. for three hours and filtered free of unreacted $P_2S_5$ to yield 710 gms.(2.0 m) of dithiophosphoric acid with a neutralization number of 154 (Theory: 158).

B. Synthesis Of Dithiophosphoric Ester-Alcohol From The Dithiophosphoric Acid Prepared In (A)

356.0 gms. (1.00 m) of dithiophosphoric acid prepared in A was combined with 268.0 gms. (1.00 m) of a $C_{18}$ Epoxide at ambient temperature. The reaction mixture was then stirred at 90° C. for three hours, vacuum stripped and filtered to yield 460 gms (Theory: 484 gms.) of the dithiophosphoric ester-alcohol.

| Tests | Found | Theory |
| --- | --- | --- |
| % S | 12.4 | 13.2 |
| % P | 6.7 | 6.4 |

EXAMPLE III

Preparation Of Dithiophosphoric Ester-Alcohol From Mixed $P_2S_5$ Acids And A $C_8$ Epoxide

55.0 gms. (0.125 m) of dithiophosphoric acid prepared from 4-methyl-2-pentanol and 36.6 gms. (0.125 m) of dithiophosphoric acid prepared from iso- propanol were combined with 74.5 gms.(0.25 m) of a $C_{18}$ epoxide at ambient temperature, stirred at 90° C. for three hours, vacuum stripped and filtered to yield 127 gms (Theory:139 gms) of dithiophosphoric ester-alcohol.

| Tests | Found | Theory |
| --- | --- | --- |
| % S | 10.1 | 11.5 |
| % P | 5.3 | 5.6 |

EXAMPLE IV

Preparation Of Dithiophosphoric Ester-Alcohol From 4-Methyl-2-Pentanol, $P_2S_5$ And a $C_{10}$ Epoxide

110.0 gms. (0.25 m) of dithiophosphoric acid prepared from 4-methyl-2- pentanol and 45.0 gms. (0.25 m) of a $C_{10}$ Epoxide were combined at ambient temperature. The mixture was then stirred at 90° C. for 3 hours, vacuum stripped and filtered to yield 106 gms. (Theory:120 gms) of a dithiophosphoric ester-alcohol.

| Tests | Found | Theory |
| --- | --- | --- |
| % S | 12.3 | 13.3 |
| % P | 6.7 | 6.5 |

EXAMPLE V

Preparation Of Dithiophosphoric Ester-Alcohol From Dithophosphoric Acid Made From 1-Hexanol And a $C_{18}$ Epoxide

105.0 gms. (0.25 m) of dithiophosphoric acid prepared from 1-hexanol and 74.5 gms. (0.25 m) of a C-18 Epoxide were combined at ambient temperature. The mixture was then stirred at 90° C. for 3 hours, vacuum stripped and filtered to yield 137 gms. (Theory: 149.5 gms.) of a corresponding ester-alcohol.

| Tests | Found | Theory |
| --- | --- | --- |
| % S | 10.1 | 10.7 |
| % P | 5.4 | 5.2 |

EXAMPLE VI

Preparation Of Dithiophosphoric Diester-Alcohol From Dithophosphoric Acid Made From 2-Octanol And a $C_{20}$–$C_{24}$ Epoxide

124.0 gms. (0.25 m) of dithiophosphoric acid prepared from 2-octanol and 86.5 gms. (0.25 m) of a ($C_{20}$–$C_{24}$) Epoxide combined at ambient temperature. The mixture was then stirred at 90° C. for 3 hours, vacuum stripped and filtered to yield 153 gms. (Theory: 176 gms.) of corresponding ester-alcohol.

| Tests | Found | Theory |
| --- | --- | --- |
| % S | 7.6 | 9.1 |
| % P | 3.9 | 4.4 |

The following are data from tests to illustrate the effectiveness of the lubricant additives.

TEST DATA SHOWING THAT THE DITHIOPHOSPHORIC ESTER-ALCOHOLS ARE ANTIOXIDANTS

All additives were evaluated in a Bench Oxidation Test-(BOT). In the BOT, the additive (0.10% P), overbased sulfonate (0.18% Ca) and SNO-150 were heated to 175° C. under $N_2$ and a sample taken (baseline). The mixture was then stirred at 175° C. under a stream of air at 500 m./min. for six hours. Samples were taken every hour and the DIR of each sample was determined against the baseline at 1712 cm-1. The six hour DIR was used as a measure of oxidation; the smaller the value, the better the antioxidant properties.

| Bench Oxidation Test | | |
|---|---|---|
| Sample | No Additive | Six Hour DIR |
| SNO-150 + Overbased(ob) Sulfonate + No Additive | 22.0 | — |
| SNO-150 + (ob) Sulfonate + Zinc Dithiophosphate | — | 6.1 |
| SNO-150 + (ob) sulfonate + Example I | — | 6.5 |
| SNO-150 + (ob) sulfonate + Example II | — | 4.7 |
| SNO-150 + (ob) sulfonate + Example III | — | 6.6 |
| SNO-150 + (ob) sulfonate + Example IV | — | 6.4 |
| SNO-150 + (ob) sulfonate + Example V | — | 6.8 |
| SNO-150 + (ob) sulfonate + Example VI | — | 6.9 |

We claim:

1. An ashless, antioxidant lubricating oil additive, comprising the additive prepared by:

(a) reacting an alcohol selected from the group consisting of 2-octanol, isopropanol, 1-hexanol and 4-methyl-2-pentanol with phosphorus pentasulfide to form a dithiophosphoric acid intermediate;

(b) treating said dithiophosphoric acid intermediate with an epoxide represented by the formula

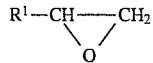

wherein $R^1$ is $CH_3(CH_2)_x$ where x is a value of about 9 to about 40.

(c) recovering said ester alcohol product lubricant oil additive.

2. The additive of claim 1 wherein said alcohol is reacted with said phosphorus pentasulfide in a ratio of alcohol to pentasulfide of about 3:1 to about 5:1.

3. The additive of claim 1 wherein said dithiophosphoric acid is treated with said epoxide in a ratio of acid to epoxide ranging from about 0.5:1.0 to about 1.5:1.0.

4. The additive of claim 1 wherein said alcohol is reacted with said phosphorus pentasulfide at a temperature ranging from about 70° C. to about 90° C. for a period of time ranging from about 1 to about 5 hours.

5. The additive of claim 1 wherein said dithiophosphoric acid is reacted with said epoxide at a temperature of about 90° C. for a period of about three hours.

6. The additive of claim 1 wherein the dithiophosphoric ester alcohol product is represented by the formulas

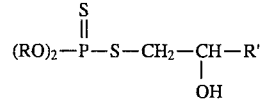

and

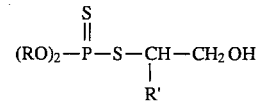

wherein R is selected from 2-octyl, isopropyl, 1-hexyl, or 4-methyl-2-pentyl and R' is $CH_3(CH_2)_x$ where x is a value of about 9 to about 40.

* * * * *